United States Patent [19]
Nojiri et al.

[11] Patent Number: 4,690,913
[45] Date of Patent: Sep. 1, 1987

[54] SILVER CATALYST FOR PRODUCTION OF ETHYLENE OXIDE FROM ETHYLENE AND PROCESS FOR PRODUCING THE CATALYST

[75] Inventors: Naohiro Nojiri, Tsuchiura; Yukio Sakai, Ami, both of Japan

[73] Assignee: Mitsubishi Petrochemical Co., Ltd., Tokyo, Japan

[21] Appl. No.: 767,831

[22] Filed: Aug. 20, 1985

[30] Foreign Application Priority Data

Aug. 21, 1984 [JP] Japan .................... 59-173884
Sep. 14, 1984 [JP] Japan .................... 59-191732
Oct. 25, 1984 [JP] Japan .................... 59-224877

[51] Int. Cl.$^4$ .................... B01J 23/02; B01J 23/04; B01J 23/50
[52] U.S. Cl. .................... 502/340; 502/347
[58] Field of Search .................... 502/340, 341, 347, 348, 502/224

[56] References Cited

U.S. PATENT DOCUMENTS

| | | | |
|---|---|---|---|
| 3,702,259 | 11/1972 | Nielsen | 117/37 R |
| 3,943,069 | 3/1976 | Antonelli et al. | 502/348 X |
| 3,962,136 | 6/1976 | Nielsen et al. | 502/347 X |
| 3,962,286 | 6/1976 | Antonelli et al. | 260/348.5 R |
| 4,007,135 | 2/1977 | Hayden et al. | 502/347 X |
| 4,066,575 | 1/1978 | Winnick | 252/475 |
| 4,212,772 | 7/1980 | Mross et al. | 252/476 |
| 4,248,740 | 2/1981 | Mitsuhata et al. | 252/463 |
| 4,342,667 | 8/1982 | Armstrong et al. | 502/347 |
| 4,356,312 | 10/1982 | Nielsen et al. | 549/534 |
| 4,414,135 | 11/1983 | Nojiri et al. | 502/224 |
| 4,415,476 | 11/1983 | Ayame et al. | 502/224 |
| 4,458,032 | 7/1984 | Rebsdat et al. | 502/348 |
| 4,471,071 | 9/1984 | Rebsdat et al. | 502/347 |

FOREIGN PATENT DOCUMENTS 58-1191 10/1983 Japan .
59-12757 1/1984 Japan .
2043481 10/1980 United Kingdom .

Primary Examiner—W. J. Shine
Attorney, Agent, or Firm—Wenderoth, Lind & Ponack

[57] ABSTRACT

A catalyst for the production of ethylene oxide from ethylene, said catalyst comprising a porous carrier composed of a molded article of a refractory material and at least silver grains deposited on the carrier, wherein (A) silver is distributed on the outside surface of the carrier and on the inner surfaces of the pores of the carrier, (B) silver grains distributed on the inner surfaces of the pores of the carrier have an average diameter of 0.05 to 0.4 micron, and (C) the loading (S) of silver on the outside surface layer of the catalyst and the loading (I) of silver on the innermost layer of the catalyst satisfy the following expression $I \geq 0.65S$;

and a process for producing a catalyst for the production of ethylene oxide from ethylene, which comprises impregnating an aqueous solution containing a silver salt and an amine as a complex forming agent in a porous carrier composed of a molded article of a refractory material, and heating the carrier with superheated steam to deposit silver on the carrier.

8 Claims, 6 Drawing Figures

Fig. 2-A
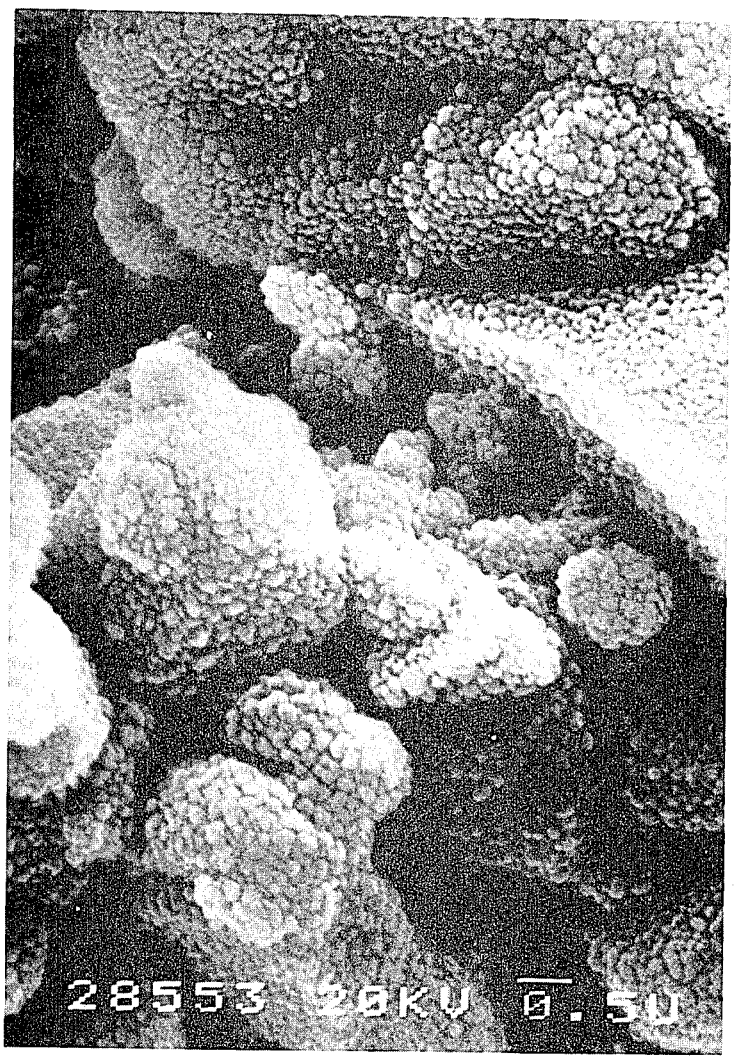

Fig. 2-B
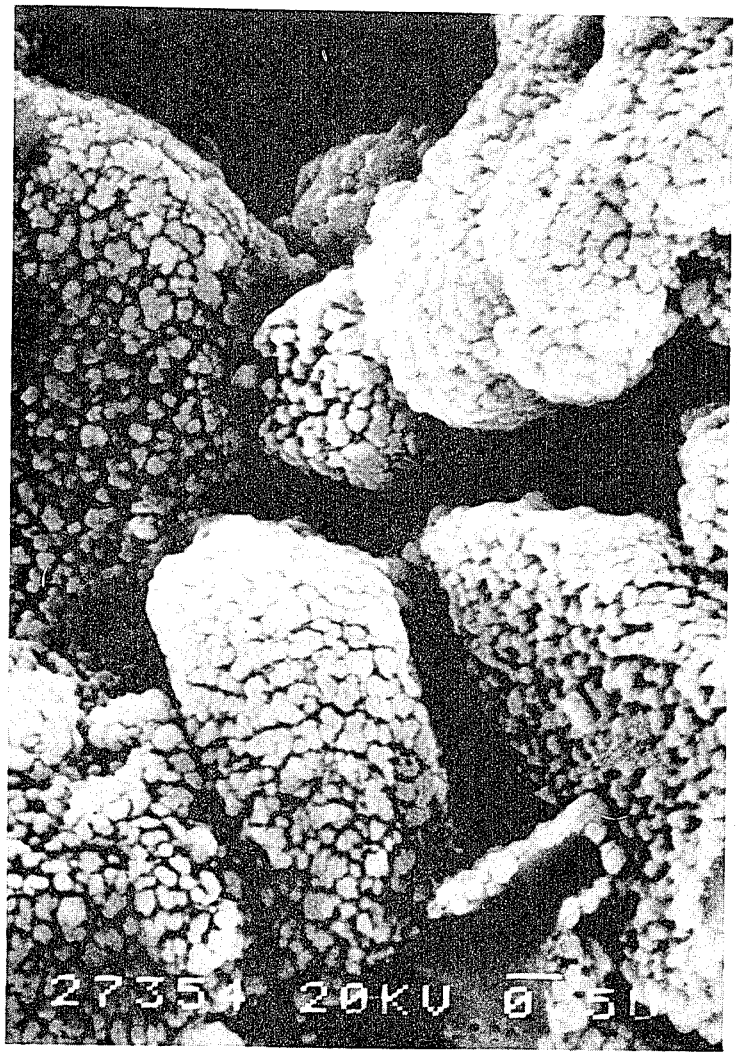

Fig. 2-C
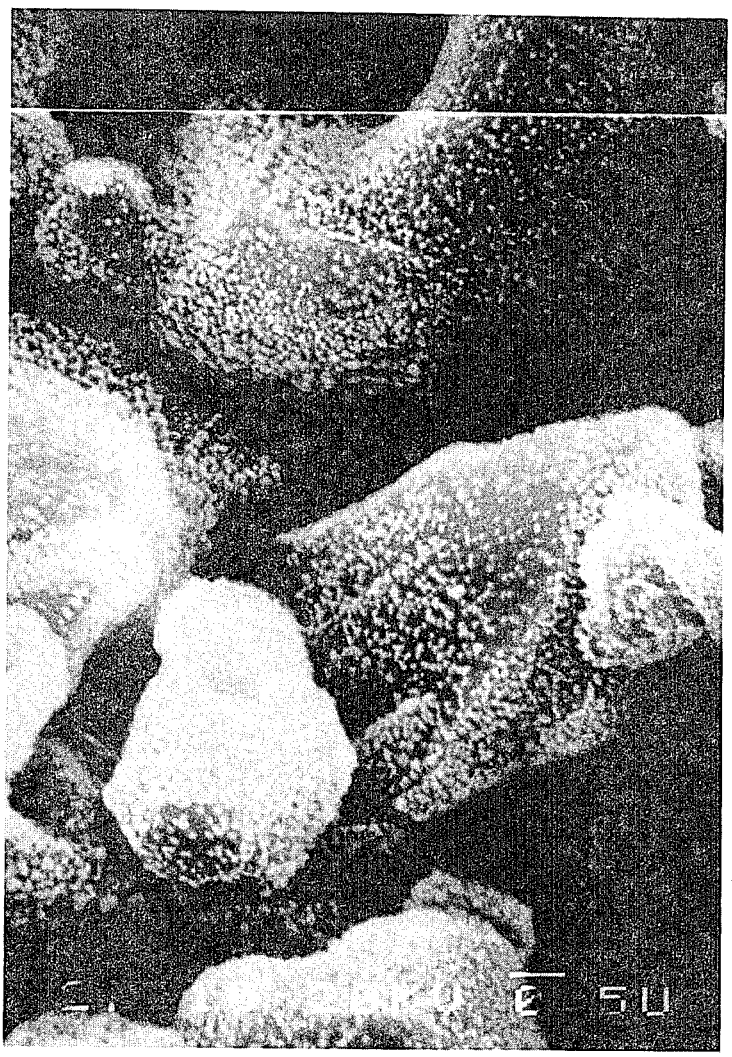

Fig. 2-D
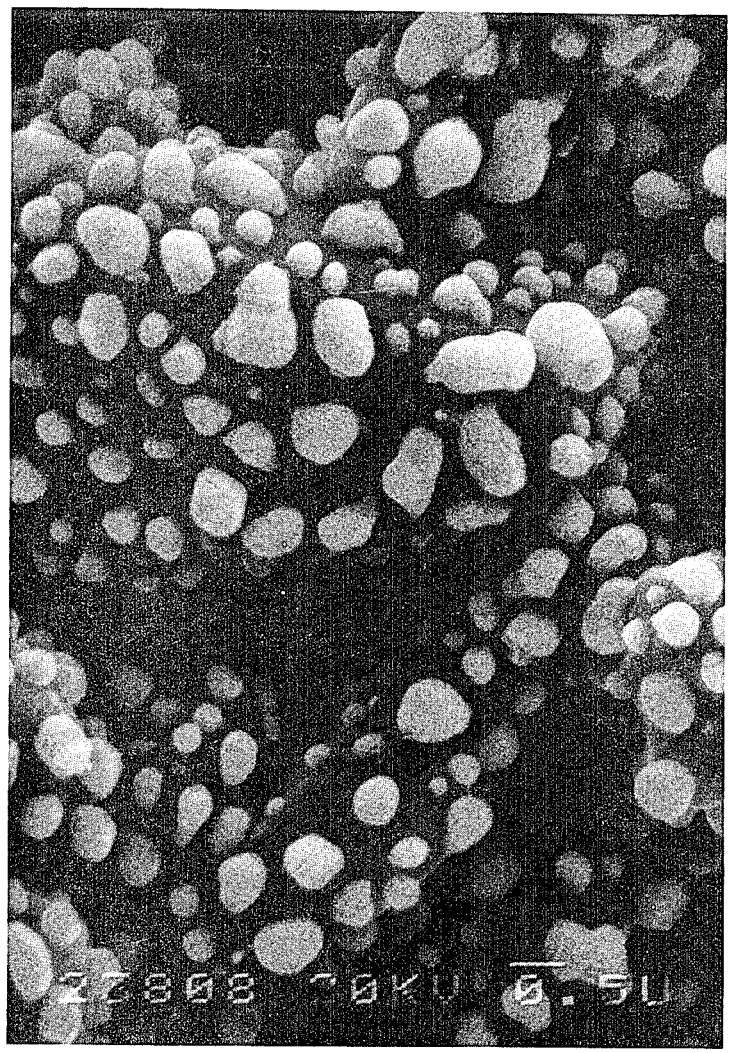

SILVER CATALYST FOR PRODUCTION OF ETHYLENE OXIDE FROM ETHYLENE AND PROCESS FOR PRODUCING THE CATALYST

BACKGROUND OF THE INVENTION

1. Field of the Invention

This invention relates to a novel silver catalyst for producing ethylene oxide by the oxidation of ethylene with molecular oxygen, and a process for producing the catalyst.

2. Description of the Prior Art

A method known for preparing a silver catalyst for use in the oxidation of ethylene with molecular oxygen comprises impregnating a porous refractory carrier with an aqueous solution of a silver salt complexed with an amine (encompassing ammonia) and heating the impregnated carrier with air or the like to deposit silver on the carrier. By using amines, the silver salt decomposed and reduced at low temperatures is converted into an amine complex, and thus can be formed into a uniform aqueous solution. Hence, fine and uniform silver grains can be deposited on a porous carrier composed of a molded article of a refractory material to give a catalyst of excellent performance.

According to the description of Japanese Patent Publication No. 22146/1980, to deposit silver from a silver salt-containing aqueous solution and make a catalyst, heating at 100° to 375° C. for 2 to 8 hours is required, and air is used as a heating medium. Investigations of the present inventors have shown that the above method of heating results in a non-uniform distribution in the amount of deposited silver within a catalyst particle, and when the heating temperature and time described in the Examples of the above-cited Japanese Patent Publication are employed, the silver grains agglomerate and grow. For example, it has been ascertained that in a catalyst having 13% by weight of Ag deposited on a carrier having a surface area of 0.4 m$^2$/g which is prepared by calcination in air at 270° C. for 2 hours, many of the deposited silver grains have a particle diameter of at least 0.4 micron, and thus, the silver grains are large and are distributed non-uniformly in each catalyst particle. For this reason, such a catalyst cannot exhibit a sufficient catalytic performance.

SUMMARY OF THE INVENTION

It is an object of this invention to provide a novel catalyst for the production of ethylene oxide from ethylene, in which silver grains deposited on a carrier are fine and uniform to give higher catalytic activity, and the amount of the silver grains deposited is very uniform from the surface layer to the inner layer of each catalyst particle, and the speed of agglomeration of the silver particles that occurs as the reaction proceeds is slow to give a long catalyst life, and a process for producing the novel catalyst.

According to this invention, there is provided a catalyst for the production of ethylene oxide from ethylene, said catalyst comprising a porous carrier composed of a molded article of a refractory material and at least silver grains deposited on the carrier, wherein (A) silver is distributed on the outside surface of the carrier and on the inner surfaces of the pores of the carrier, (B) silver grains distributed on the inner surfaces of the pores of the carrier have an average diameter of 0.05 to 0.4 micron, and (C) the loading (S) of silver on the outside surface layer of the catalyst and the loading (I) of silver on the innermost layer of the catalyst satisfy the following expression $$I \geq 0.65 S.$$

According to this invention, there is also provided a process for producing a catalyst for the production of ethylene oxide from ethylene, which comprises impregnating an aqueous solution containing a silver salt and an amine as a complex forming agent in a porous carrier composed of a molded article of a refractory material, and heating the carrier with superheated steam to deposit silver on the carrier.

The process of this invention has the advantage that the catalyst having the above characteristic features and being free from the defects of the prior art can be produced particularly at low temperatures within short periods of time.

BRIEF DESCRIPTION OF THE ACCOMPANYING DRAWINGS

FIG. 1 shows temperature elevation patterns of the catalyst of this invention (Example 1) and a control catalyst obtained by heating in air (Comparative Example 1); FIGS. 2-A to 2-D are scanning electron micrographs (magnification 10,000×), FIG. 2-A showing the porous surface of the interior of a catalyst particle in the catalyst of this invention (Example 1), FIGS. 2-B and 2-C respectively showing the outside surface layer and the surface of the pores inside of a catalyst particle in the control catalyst (Comparative Example 1), and FIG. 2-D showing the porous surface of the inside of a catalyst particle in a control catalyst (Comparative Example 2); and FIG. 3 shows the distribution of silver in a catalyst particle in the catalyst of this invention (Example 1) and the control catalyst (Comparative Example 1).

DETAILED DESCRIPTION OF THE INVENTION

Figure 1:
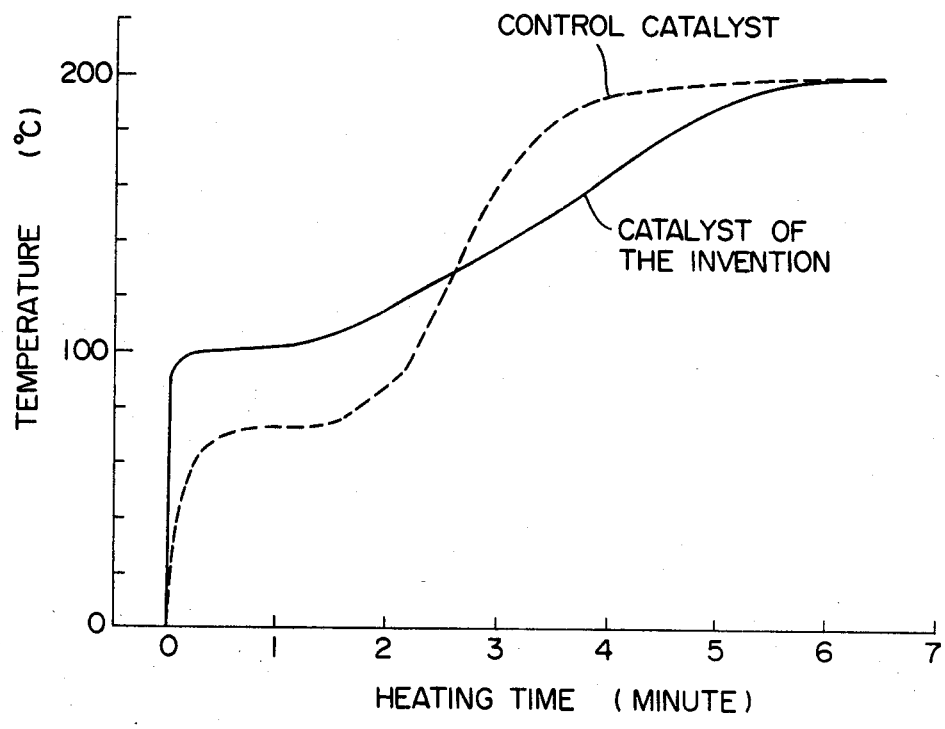

The catalyst of this invention for the production of ethylene oxide from ethylene, which has the aforesaid characteristics and advantages, can be produced by impregnating an aqueous solution containing a silver salt and an amine as a complex forming agent in a porous carrier composed of a molded article of a refractory material, and heating the carrier with superheated steam to deposit silver on the carrier.

In the process of this invention, silver is deposited on the carrier preferably by bringing the porous carrier impregnated with the aqueous solution containing a silver salt and an amine as a complex forming agent into contact with superheated steam at a temperature of at least 120° C. while it contains at least a part of the aqueous solution. Particularly, it is advantageous that silver is deposited on the carrier by contacting the porous carrier impregnated with the aqueous solution containing a silver salt and an amine as a complex forming agent, with superheated steam at 120° to 500° C., preferably 120° to 300° C., above all 150° to 260° C., while the ratio of removal of the aqueous medium in the aqueous solution is 0 to 70% by weight, preferably 0 to 50% by weight. That is, it is particularly advantageous that heating of the impregnated carrier with the superheated steam be conducted under the condition that at least 30% by weight; preferably at least 50% by weight, of the aqueous medium of the aqueous solution remains with the carrier, to at least substantially dry the aqueous medium and decompose the silver salt to deposit silver on the carrier.

The silver salt that can be used in the process of this invention may be any silver salt which when formed into a complex soluble in an aqueous medium with the amine (including ammonia) decomposes at a temperature of not more than 500° C., preferably not more than 300° C., especially preferably not more than 260° C., to deposit silver. Examples of such a silver salt are silver oxide, silver nitrate, silver carbonate and silver carboxylates such as silver oxalate and silver acetate. The silver carboxylates are preferred.

The amine as the complex forming agent may be any amine which acts as a ligand for maintaining silver in solution. Examples include pyridine, acetonitrile, ammonia and primary or secondary amines having 1 to 6 carbon atoms. Examples of preferred amines are ammonia, monoamines such as pyridine and butylamine, alkanolamines such as ethanolamine, alkylene diamines having 2 to 4 carbon atoms, and polyamines. Diamines having 2 to 4 carbon atoms are especially preferred, and ethylenediamine and 1,3-propane-diamine are suitable. A combination of ethylenediamine and 1,3-propanediamine is most preferred. The combined use of the amine with another amine or another compound, for example, a tiny amount of dimethylformamide is also effective. The silver salt and the amine are formed into a uniform solution, preferably a uniform aqueous solution. Water-miscible organic solvents such as alcohol, or a mixture thereof with water may also be used to prepare the solution. The resulting solution is impregnated into the porous refractory carrier.

Examples of the porous refractory carrier are alpha-alumina, silicon carbide, titania, zirconia and magnesia. An alpha-alumina carrier having a surface area of 0.01 to 2 m$^2$/g, preferably 0.2 to 1.2 m$^2$/g, particularly 0.2 to 0.7 m$^2$/g, a pore volume of 0.2 to 0.5 ml/g and an average pore diameter of 0.1 to 20 microns is preferred. The porous refractory carrier is in the form of a molded article of the refractory material having a size of about 4 to 15 mm which is, for example, spherical, ring-like, or cylindrical.

The impregnating operation is carried out by methods known to those skilled in the art. As required, such operations as pressure reduction, heating, and rotation spraying, and devices therefor are used. The concentration of silver and the amount of the amine in the amine in the impregnating solution are adjusted so that the amount of silver deposited becomes 5 to 20% by weight based on the finished catalyst. The amine is added in an amount sufficient to complex the silver salt (usually, two amino groups correspond to one mole of silver). Usually, the amine is added in an amount 10 to 30% above the equivalent amount.

In the process of this invention, the porous carrier composed of the molded article of the refractory material is impregnated with the aqueous solution containing the silver salt and the amine as a complex forming agent, and then heated over superheated steam, preferably at a temperature of at least 120° C. to substantially complete the deposition of silver on the carrier.

The process of this invention is therefore clearly different from the process for producing a catalyst for the production of ethylene oxide disclosed in Japanese Laid-Open Patent Publication No. 1191/1978, which comprises impregnating a carrier with an aqueous solution of a thermally decomposable silver complex compound, a sodium compound and a heavy alkali metal compound, treating the carrier with steam, especially saturated steam, until the silver compound begins to decompose with care taken not to cause loss of water from the impregnated carrier, and then heating the carrier in a gas such as $CO_2$, $N_2$ or air at a temperature of 150° to 300° C. until the carrier attains a constant weight.

In the present invention, the deposition of silver from an impregnating aqueous solution of silver oxalate complexed with 1,3-propanediamine takes place at a temperature in the vicinity of 120° C. If only the amount of heat required to complete the silver deposition reaction is supplied from superheated steam, the catalyst can be prepared by heating with superheated steam at that temperature.

Agglomeration of silver deposited on the carrier occurs vigorously particularly when the heating is done in air at a high temperature of more than 200° C. The heating of the impregnated carrier in superheated steam in the present invention offers the advantage that the agglomeration of the deposited silver grains is very effectively inhibited.

However, in superheated steam, too, the silver grains tend to be agglomerated to a greater extent as the temperature of the superheated steam becomes higher beyond 260° C. or the heating time becomes longer. It is preferred therefore to control the conditions so as to avoid agglomeration.

Advantageously, the amount of silver deposited is 5 to 20% by weight, preferably 8 to 50% by weight, based on the entire catalyst.

It has been found in accordance with this invention that the diameter (the shorter diameter when the grains are not spherical) of typical silver grains deposited on the carrier depends mainly upon the ratio of Ag deposited and the surface area of the carrier. It can be said that when in the present invention, the ratio of Ag deposited is in a preferred range of 8 to 15% and the surface area of the carrier is in a range of 0.2 to 0.6 m$^2$/g, the diameter, d (microns), of the silver grains is nearly proportional to [the amount of Ag deposited]$^{0.2}$ multiplied by [the surface area of the carrier]$^{-1.2}$.

Japanese Patent Publication No. 33565/1978 discloses a process for producing a catalyst which comprises (a) impregnating a thermally decomposable silver salt in an inert particulate support, (b) drying it at a temperature not exceeding 160° C., (c) passing superheated steam so that its temperature reaches a selected point within a range of 270° to 350° C., (d) substituting air for the steam at the aforesaid temperature over at least 1 hour, and (e) passing heated air for at least 30 minutes at the same temperature. This process requires a very complex and time-consuming heat-treatment during the catalyst preparation, and only after this heat-treatment, a good catalyst can be obtained.

The above-cited Japanese patent document does not describe the use of a silver salt complexed with an amine as the thermally decomposable silver salt. Accordingly, from the standpoint of using the amine complex in the present invention, the process described in the Japanese patent document employs the undesirable high temperature, long time heat-treatment. For example, while the heat-treatment in accordance with this invention is carried out at a temperature in the range of 150° to 260° C. for a period of as short as about 15 minutes, the process described in the Japanese patent document requires the superheated steam treatment at 270° to 350° C., preferably 290° to 320° C., and the heated air treatment for at least 1.5 hours. If the amine complex of the silver salt used in this invention is subjected to this treatment, the deposited silver grains are remarkably agglomerated and distributed non-uniformly within the catalyst particle. Presumably, the agglomeration is due mainly to the high-temperature air treatment, and the non-uniform distribution is due mainly to the large temperature difference between the temperature (about 100° C.) of the impregnated carrier and the temperature of the superheated steam at the time of evaporation of water (because of this temperature difference, evaporation of water occurs too vigorously). In addition, in the process of the Japanese patent document, the operation of drying the impregnated carrier in the dry state for a sufficient long period of time (1 to 10 hours) is essential prior to the heat-treatment with superheated steam. This method of treatment is quite different from the heating of the impregnated carrier in the present invention with superheated steam while the impregnated carrier still contains water.

It is preferred that in the process of this invention, at least one element as a cationic component (D) selected from the group consisting (D-1) lithium, sodium, potassium, rubidium and cesium (alkali metal elements), (D-2) calcium and barium (alkaline earth metal elements), and (D-3) thallium, tin and antimony is deposited on the porous carrier in addition to the silver grains.

As the cationic component, (i) at least one alkali metal element selected from the group consisting of lithium, sodium, potassium, rubidium and cesium, or (ii) a combination of at least one alkali metal element (i) with barium is preferred.

As the cationic component of group (i), a combination of sodium and cesium, a combination of sodium and potassium, a combination of sodium and rubidium, a combination of potassium and cesium, and a combination of lithium and cesium are preferred. As the group (ii), a combination of the two elements mentioned above with barium, especially a combination of sodium, cesium and barium, is preferred.

In the process of the present invention, it is more preferred to deposit at least one element as (D) a cationic component selected from the group consisting of (D-1) at least one alkali metal element selected from the group consisting of lithium, sodium, potassium, rubidium and cesium, (D-2) at least one alkaline earth metal element selected from calcium and barium, and (D-3) at least one element of thallium, tin and antimony, and at least one element as an anionic component (E) selected from the group consisting of fluorine, chlorine and bromine on the porous carrier in addition to the silver grains.

To deposit the cationic component on the porous carrier, it is generally desirable to add it in the form of a water-soluble compound, generally a nitrate, halide, hydroxide, carbonate, bicarbonate or carboxylate. An oxide may also be used. Specific examples of the water-soluble compound of the cationic component are lithium carbonate, sodium carbonate, sodium bicarbonate, sodium acetate, potassium nitrate, cesium nitrate, cesium chloride, rubidium nitrate, barium nitrate, barium hydroxide, barium oxide, calcium hydroxide, calcium oxide, thallium chloride, tin bromide and antimony chloride.

Suitable amounts of the above compounds may be added to the impregnating solution at the same time or individually to deposit them on the porous carrier. These additional compounds may be deposited on the carrier before or after the deposition of silver. Deposition of these cationic components by heating may also be carried out by known methods. But the use of superheated steam is preferred because the cationic component is distributed uniformly in the catalyst particles and this favors the performance of the catalyst.

The anionic component may be added in the same way as in the case of the cationic component. Desirably, the anionic component is generally added in the form of a water-soluble compound. It is preferred to add it in the form of a salt with the above cationic component, that is, an alkali metal element such as lithium, sodium, potassium, rubidium and cesium, an alkaline earth metal element such as barium or calcium, or thallium, tin or antimony. An ammonium salt may also be used. Some examples are lithium bromide, sodium chloride, potassium fluoride, cesium chloride, thallium chloride, and ammonium chloride.

A suitable amount of the above component is added to the impregnating solution, and the anionic compound may be deposited on the porous carrier at the same time as the deposition of silver.

It is also possible to deposit the anionic component before or after the deposition of silver. The deposition of the anionic component by heating may also be performed by known methods. But the use of superheated steam is preferred because the anionic component is distributed uniformly in the catalyst particles and this favors the performance of the resulting catalyst.

In the catalyst of this invention, the cationic component and the anionic component which modify silver as a reactive species and improves the selectivity of the reaction are uniformly distributed within each catalyst particle, and these components uniformly modify silver. Hence, the selectivity of ethylene oxide formation is increased.

The process of this invention thus gives a catalyst for the production of ethylene oxide from ethylene. This catalyst comprises a pourous carrier composed of a molded article of a refractory material and at least silver grains deposited on the carrier, wherein (A) silver is distributed on the outside surface of the carrier and on the inner surfaces of the pores of the carrier, (B) silver grains distributed on the inner surfaces of the pores of the carrier have an average diameter of 0.05 to 0.4 micron, preferably 0.1 to 0.3 micron, and (C) the loading (S) of silver on the outside surface layer of the catalyst and the loading (I) of silver on the innermost layer of the catalyst satisfy the following expression $$I \geq 0.65S, \text{ preferably } I \geq 0.7S.$$

The average diameter of the silver grains distributed on the inner surfaces of the pores of the carrier in (B) above can be measured by observing the section of the catalyst particle by a scanning electron microscope. For example, with regard to silver grains clearly observed by a scanning electron micrograph (for example 10,000×), the diameters (the shorter diameters when the grains are not spherical) of about 30 larger silver grains and those of about 30 smaller grains are read, and the total of the diameters read is divided (averaged) by the total number (60) of the grains. This gives the average diameter.

The loading (S) of silver on the outer surface layer of the catalyst of this invention and the loading (I) of silver on the innermost layer of the catalyst defined in (C) above can be determined by gradually shaving off the catalyst from the outer surface to the inner layer of the catalyst of this invention, and measuring the content (weight) of silver per unit weight (for example, 1 gram) of the catalyst so shaven.

In the present invention, the ouside surface layer of the catalyst denotes a portion having a weight of about 5% by weight (in the range of about 4–6%) shaven as uniformly as possible from the ouside surface of one catalyst (carrier) particle toward its inner layer when the weight of one catalyst particle is taken as 100%. The innermost layer of the catalyst denotes an inner layer (innermost layer) of the catalyst particle which is left after about 60% on an average (in the range of about 50 to 70%, preferably 55 to 65%) has been shaven off from the outside surface of the catalyst particle (carrier) toward its inner layer as uniformly as possible.

A simple method of measuring S and I is to take 30 to 50 catalyst particles, measuring their entire weight, rotating the particles in a rotating vessel to shave off the catalyst particles from the surface toward the inside layer, and determine S and I as average values of the catalyst particles in accordance with the above method.

In the catalyst of this invention, the following relation is satisfied between the loading (S) of silver of the outside surface layer of the catalyst and the loading (I) of silver of the innermost layer of the catalyst.

$$I \geqq 0.65S,$$

preferably $I \geqq 0.7S$.

In the formula $I \geqq 0.65S$, I is preferably larger than 0.65S.

It is evident therefore that in the catalyst of this invention, the silver grains are very uniformly deposited ranging from the surface layer of the catalyst particle toward its innermost layer.

It is evident from the average diameter specified in (B) above that in the catalyst of this invention, the silver grains distributed on the inner surfaces of the pores of the catalyst carrier are very fine and uniform and do not substantially contain large agglomerated masses.

The silver grains deposited on the carrier in this invention have an average particle diameter of preferably as fine as not more than 0.3 micron, especially not more than 0.2 micron, and therefore, the catalyst has high activity. Furthermore, since the distribution of the silver grains in the catalyst particles is very uniform as typically shown by $I \geqq 0.7S$, preferably $I \geqq 0.75S$, the speed of agglomeration of the silver grains which occurs as the reaction proceeds is slow, and the active lifetime of the catalyst is prolonged. In addition, in preferred embodiments, the cation component and the anionic component which modify silver as a reactive species and improve the selectivity of the reaction are used.

Thus, in one preferred embodiment of the present invention, there is provided a catalyst comprising the aforesaid porous carrier composed of a molded article of a refractory material and deposited on the carrier, not only the silver grains but also at least one element as a cationic component (D) selected from the group consisting of (D-1) at least one alkali metal element selected from the group consisting of lithium, sodium, potassium, rubidium and cesium, (D-2) at least one alkaline earth metal element selected from calcium and barium and (D-3) at least one element of thallium, tin and antimony.

The especially preferred cationic component (D) is
(i) at least one alkali metal element (D-1) selected from the group consisting of lithium, sodium, potassium, rubidium and cesium, or
(ii) a combination of at least one alkali metal element (D-1) with barium (D-2).

According to another preferred embodiment, the catalyst of this invention comprises the aforesaid porous carrier composed of a molded article of a refractory material and deposited on the carrier not only the silver grains but also at least one element as a cationic component (D) selected from the group consisting of (D-1) at least one alkali metal element selected from the group consisting of lithium, sodium, potassium, rubidium and cesium, (D-2) at least one alkaline earth metal element selected from calcium and barium, and (D-3) at least one element of thallium, tin and antimony, and at least one element as an anionic component (E) selected from the group consisting of fluorine, chlorine and bromine.

Preferably, the cationic component is at least one of lithium, sodium and barium, and/or at least one of potassium, rubidium and cesium.

One particularly preferred catalyst of this invention is one in which the cationic component is deposited on the outside surface of the carrier and on the inner surfaces of the pores of the carrier, and the loading (Sc) of the alkali metal element as the cationic component on the inner surface of the pores in the outside surface layer of the catalyst and the loading (Ic) of the alkali metal element as cationic component on the inner surfaces of the pores in the innermost layer of the catalyst have the following relation.

$$Ic \geqq 0.2Sc$$

The Sc and Ic can be measured by the same method as the method of measuring S and I with regard to the distribution of the silver grains in the catalyst.

When at least one cationic component of lithium, sodium and barium is deposited on the outside surface of the carrier and the inner surfaces of the pores of the carrier, the loading (Sc) of lithium and/or sodium on the inner surfaces of the pores in the outside surface layer of the catalyst and the loading (Ic) of lithium and/or sodium on the inner surfaces of the pores in the innermost layer of the catalyst have the following relation.

$$Ic \geqq 0.3Sc, \text{ preferably } Ic \geqq 0.4Sc.$$

When at least one alkali metal element of potassium, rubidium and cesium is deposited on the outside surface of the carrier and on the inner surfaces of the pores of the carrier, it is especialy advantageous that the loading (Sc) of the alkali metal element on the inner surfaces of the pores in the outside surface layer of the catalyst and the loading (Ic) of the alkali metal element on the inner surfaces of the pores in the innermost layer of the catalyst have the following relation.

Ic ≧ 0.5Sc, preferably Ic ≧ 0.6Sc.

The preferred amount of the cationic component based on the entire catalyst is
(1) 0.1 to 1% by weight for sodium and lithium,
(2) not more than 0.1% by weight for potassium, rubidium, cesium and thallium, and
(3) not more than 1% by weight for barium.

The preferred amount of the anionic component deposited is not more than 0.05% by weight.

The amount of sodium as the cationic component is preferably more than 50 ppm (mg/kg of catalyst) based on the catalyst, particularly from 500 ppm to 1% by weight. When the amount of sodium is too large, both the activity and selectivity of the resulting catalyst are reduced, and if it is too small, the dispersion of Ag grains on the carrier is worse than in the catalyst of this invention when the catalyst is observed under a scanning electron microscope, and consequently, the catalytic activity is low and the effect of adding halogen is not sufficiently manifested.

The preferred amount of cesium is smaller than sodium, and is preferably 10 ppm to 0.5% by weight, more preferably 15 ppm to 0.1% by weight. If it is too large, the activity of the catalyst is markedly reduced, and if it is too small, the effect of halogen cannot be manifested fully.

The preferred amount of barium to be added is more than 10 ppm but not more than 1% by weight, especially preferably 20 ppm to 3000 ppm. If it is too small, there is no effect of adding barium. If it is too large, a precipitate may form in the impregnating solution or the impregnating step becomes complex. Moreover, the activity of the catalyst is lowered.

The amount of the halogen selected from fluorine, chlorine and bromine is suitably 5 ppm to 0.1% by weight, preferably 7 ppm to 0.07% by weight, based on the catalyst. If it is added in too large an amount, it shows a poisoning action and drastically reduces the performance of the catalyst. In the present invention, by adding a minute amount of halogen, which shows a poisoning action when added in large amounts, with the cationic component such as sodium, cesium and barium, a silver catalyst having an increased performance can be obtained.

When both the cationic component and the anionic component are used, a small amount of lithium, rubidium, potassium or thallium may be added in addition to sodium, cesium and barium.

The above catalyst ingredients are used as a supported catalyst mainly for economic reasons and in view of the catalyst life. A porous refractory material is used as the carrier, and preferably has a BET surface area of 0.1 to 5 m$^2$/g and a pore volume of at least 0.2 ml/g. A porous refractory material composed mainly of alpha-alumina is preferred.

When sodium, cesium and barium as the cationic component and the halogen as the anionic component are to be deposited, the depositions of the cationic component and the anionic component may be effected simultaneously or separately, and in various modes in any desired stages of the catalyst preparation. For example, the depositions of the cationic and anionic components may be performed before, during or after the impregnation of the silver compound. In order to secure the uniformity of the impregnating solution and to simplify the catalyst preparing process, it is most preferred to impregnate the sodium component before the deposition of the silver compound and impregnate barium, cesium and halogen at the same time as the impregnation of the silver compound.

Figure 3:
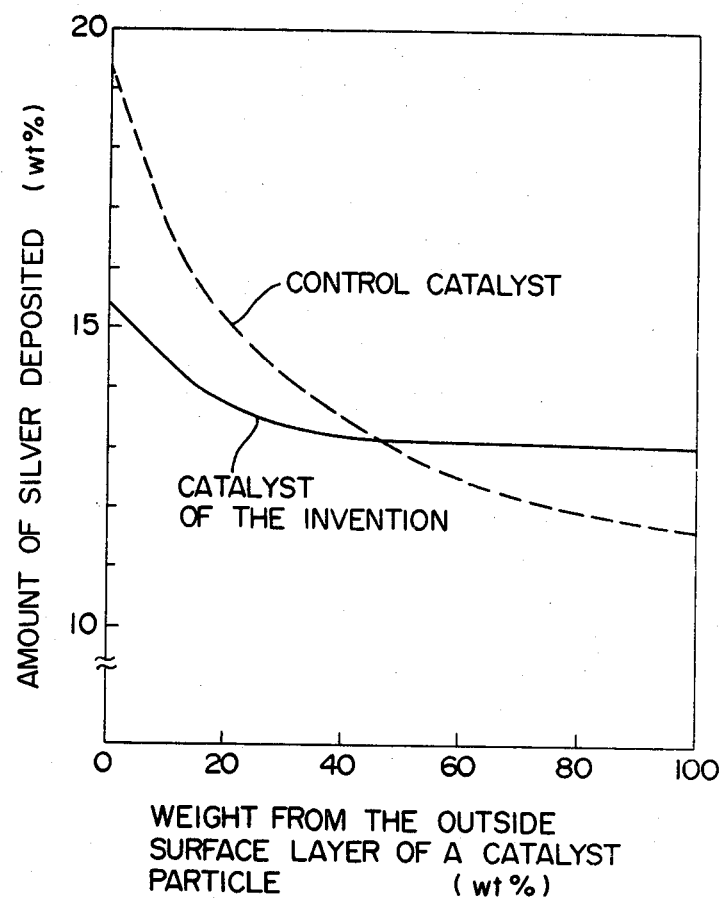

According to this invention, when the impregnated carrier is at a low temperature, superheated steam rapidly raises its temperature and uniformly heats the entire carrier layer, as shown in FIG. 1. Usually in the process of this invention for producing the catalyst, the evaporation of water and the deposition of silver by the decomposition of the silver complex take place during the heating step. The process of this invention is superior to the prior art in that the superheated steam induces the evaporation of water and the deposition of silver uniformly either simultaneously or separately. As a result, the deposited silver grains are fine as shown in FIG. 2-A, and as shown in FIG. 3, silver and the other additive components are distributed uniformly. The catalysts produced by the present invention therefore have high activity, good selectivity and a long lifetime.

Superheated steam having a pressure in the vicinity of normal atmospheric pressure is practically feasible and can be used as the superheated steam used in the present invention. It has a temperature of 120° to 500° C., especially 120° to 300° C., especially preferably 150° to 260° C. The heating time is preferably about 1 minute to about 3 hours, but is preferably shorter in view of the practical feasibility and performance of the catalyst. Usually, a period of 3 minutes to 15 minutes is most preferred. The shortest time required is determined depending upon the amount of the impregnated carrier to be heated, the temperature of the steam and the flow rate of the steam. Steam flow speeds of 0.3 m/sec to 5 m/sec are preferred in view of the performance and practical feasibility of the catalyst.

Heating with superheated steam in this invention may be carried out as follows:

The impregnated carriers are laid in a single layer or stacked in a multiplicity of layers in the form of a fixed bed or a moving bed, and superheated steam may be passed upwardly, downwardly or sideways through the layer or layers. Since the entire layers can be heated at a uniform temperature by the superheated steam, there is no non-uniformity of silver distribution among the layers. Thus, from a practical viewpoint, heating of multiple layers is economical. Nitrogen, air, etc. may be included in some amount into the superheated steam. Steam at the outlet contains amines and other decomposition products formed by the decomposition of the silver salt, and to prevent accumulation of these compounds, some amount of steam should be purged. Basically, however, recycling of superheated steam is possible and economical. For example, 90% of the superheated steam initially fed may be recycled although this amount may vary depending upon the amount of the steam and the amount of the impregnated carrier.

It is preferred in the process of this invention that the porous carrier impregnated with the aqueous solution containing the silver salt and the amine as a complex forming agent and optionally the cationic component and/or the anionic component is heated with superheated steam either as such or after removing the excess of the impregnating solution, while the ratio of removal of the aqueous medium from the aqueous solution reaches 0 to 70%, preferably 0 to 50% by weight; or the impregnated carrier is dried for example in a current of air at a temperature of not more than 100° C. and then heated with superheated steam by the method described above, thereby to deposit silver on the carrier.

The reaction of converting ethylene into ethylene oxide by using the catalyst of this invention can be performed by a conventional operating procedure. For example, the pressure is 1 to 35 kg/cm$^2$, and the temperature is 180° to 300° C., preferably 200° to 260° C. The proportion of ethylene is 1 to 40% by volume, and the proportion of oxygen is 1 to 20% by volume. Generally, it is preferred to use a fixed proportion, for example 20 to 70% by volume, of a diluent such as methane. Oxygen is supplied in the form of air or as industrial oxygen. The addition of a reaction modifier, such as ethylene dichloride can prevent the formation of hot spots in the catalyst and serves to improve the performance, especially selectivity, of the catalyst greatly. The preferred amount of the reaction modifier is several ppm (by weight) to several tens of ppm.

The following Examples and Comparative Examples illustrate the present invention.

EXAMPLE 1

Na$_2$CO$_3$ (26.9 g) was dissolved in 1 liter of water, and 1 kg of an alpha-alumina carrier (ring-like with a size of 8 $\phi$×3 $\phi$×8 mm; surface area 0.5 m$^2$/g; pore volume 0.4 ml/g) was immersed in the solution. The excess of the solution was removed by permitting it to drip, and then the impregnated carrier was dried on superheated steam at 140° C. for 15 minutes.

Separately, 248 g of AgNO$_3$ was dissolved in 1 liter of water and 148 g of potassium oxalate (K$_2$C$_2$O$_4$.H$_2$O) was dissolved in 1 liter of water. The solutions were mixed, and heated to 60° C. in a water bath to obtain a white precipitate of silver oxalate. After filtration, the precipitate was washed with distilled water to remove potassium from the precipitate. Separately, 21.7 g of 1,3-propanediamine and 79.1 g of ethylenediamine were dissolved in water to prepare 200 ml of an aqueous solution. With ice cooling, the aqueous solution was added little by little to the silver oxalate precipitate to prepare a silver oxalate-amine complex solution. The solution was then mixed with 40 ml of an aqueous solution containing 1.49 g of barium nitrate and 0.234 g of cesium chloride. The mixture was transferred to a rotary evaporator. The above alpha-alumina carrier impregnated with NA$_2$CO$_3$ and dried was added to the above mixture, and an impregnating operation was performed at 50° C. with rotation. The pressure was reduced (100 mmHg) at the early stage of the impregnating operation. The pressure was returned to normal atmospheric pressure, and 5 minutes later, the impregnated alpha-alumina carrier was taken out. The alpha-alumina carrier was heated with superheated steam at 200° C. for 10 minutes by passing the steam at a rate of 2 m/sec to prepare a catalyst in accordance with this invention.

The amounts of Ag, Na, Ba, Cs and Cl deposited were 13.5%, 0.4%, 670 ppm, 158 ppm, and 42 ppm, respectively.

FIG. 1 (solid line) shows the heating curve obtained at this time. It is seen from the heating curve that the impregnated carrier was rapidly heated with superheated steam to the boiling temperature of water. Presumably, water was evaporated from the entire surface of the carrier, and a uniform distribution of the catalyst ingredients could be obtained. Thereafter, until the carrier is heated to 200° C., the evaporation of water and the decomposition of the silver complex took place continuously.

FIG. 2-A is a scanning electron micrograph (magnification 10,000×) of the catalyst prepared. The silver grains which were fine and uniform were deposited on the inner surfaces of the pores of the carrier. The distribution of silver shown in FIG. 2-A was maintained over the entire catalyst particles, and the average diameter of the silver grains was 0.15 micron. Almost all of the silver grains had a diameter within the range of 0.05 to 0.3 micron. The catalyst had a BET surface area of 0.95 m$^2$/g.

FIG. 3 (solid line) shows a distribution of the loading of silver in the catalyst particle. The loadings of AG, Cs and Na in a portion measuring up to 6% by weight from the outside surface of the catalyst particle toward its interior were 15.0%, 177 ppm, and 4350 ppm, respectively. The loadings, I, I$_{Cs}$ and I$_{Na}$, in the interior of the catalyst particle in a portion measuring at least 60% by weight from the outside surface toward the inside were 13.0% ppm, 134 ppm, and 3500 ppm. Accordingly, I, I$_{Cs}$ and I$_{Na}$ were calculated to be about 0.87S, 0.76S$_{Cs}$ and 0.835S$_{Na}$. This shows that the individual ingredients were uniformly distributed from the outside layer to the innermost layer of each catalyst particle.

The catalyst was crushed to a size of 4 to 9 mesh, and 5 ml of it was filled in a steel reaction tube having an inside diameter of 20 mm. A reaction gas composed of 30% by volume of ethylene, 8% by volume of oxygen, 2 ppm of vinyl chloride and the remainder being nitrogen was passed through the reaction tube under a pressure of 18 kg/cm$^2$—G at an SV of 4000 h$^{-1}$. Immediately after the reaction gas was fed through the catalyst layer, the catalyst began to act. The reaction was carried out for 1 week at a bath temperature of 212° C. The conversion of oxygen was 40%, and the selectivity of ethylene oxide was 81.7%. After the reaction, the catalyst had a BET surface area of 0.84 m$^2$/g. To maintain an oxygen conversion of 40% during a continuous operation for 1.5 months, the bath temperature was raised by 2° C., but there was no change in selectivity.

EXAMPLES 2-6

Example 1 was repeated except that barium nitrate was not added, and the temperature of the superheated steam and the time of its passing, etc. during the final heating were changed as shown in Table 1. Table 1 summarizes the I/S ratios of the resulting catalysts, and the results of the catalyst carried out as in Example 1. The loadings of Ag, Na, Cs and Cl were 13.5% by weight, 0.4% by weight, 158 ppm, and 42 ppm, respectively. In the table, T$_{40}$ and S$_{40}$ show the bath temperature (°C) at which the oxygen conversion was 40%, and the selectivity (%), respectively.

TABLE 1

| Example | Temperature × time × flow rate of superheated steam | I/S | T$_{40}$ | S$_{40}$ |
|---|---|---|---|---|
| 2 | 200° C. × 10 min. × 2 m/s | 0.82 | 213 | 81.4 |
| 3 | 200 × 180 × 2 | 0.82 | 213.5 | 81.0 |
| 4 | 150 × 10 × 2 | 0.70 | 210 | 80.8 |
| 5 | 230 × 8 × 2 | 0.85 | 213 | 81.7 |
| 6 | 300 × 8 × 2 | 0.80 | 214 | 80.6 |

After the catalyst of Example 2 was used continuously for three months, T$_{40}$ was 218° C., and the S$_{40}$ was 80.8%.

EXAMPLES 7-8

Ag-CsCl-containing catalysts were prepared in the same way as in Example 1 except that the same alpha-alumina carrier as used in Example 1 but not having sodium carbonate supported thereon was used; that barium nitrate was not added, and that the time during which superheated steam was passed was changed as shown in Table 2. The amounts of silver and CsCl deposited were 13.5% by weight and 200 ppm, respectively.

Using the resulting catalysts, the same oxidation reaction of ethylene as in Example 1 was carried out. The results are also shown in Table 2.

TABLE 2

| Example | Temperature × time × flow rate of superheated steam | I/S | $T_{40}$ | $S_{40}$ |
|---|---|---|---|---|
| 7 | 200° C. × 5 min. × 2 m/s | 0.75 | 215 | 80.0 |
| 8 | 200° C. × 120 min. × 2 m/s | 0.74 | 215 | 79.3 |

COMPARATIVE EXAMPLE 1

This comparative example serves to clarify the difference between the catalyst of the present invention and a catalyst prepared by a short-time air heating method in accordance with another invention of the present inventors.

Example 2 was repeated except that the final heating was carried out by passing heated air at 200° C. for 10 minutes at a flow rate of 21 m/sec instead of using superheated steam at 200° C. A catalyst having the same composition as in Example 2 was obtained. Its heating curve is shown by a broken line (control catalyst) in FIG. 1. As shown by the broken line in FIG. 1, the temperature rising rate was slower in the initial stage of heating than in the case of using superheated steam (the solid line in FIG. 1), and a constant rate period of drying at a temperature below the boiling temperature proceeded. It is presumed that in this state the drying occurred mainly on the outside surfaces of the carrier particles, and therefore, the catalyst ingredients moved to the outside surfaces of the particles. Thereafter the decomposition of the silver salt complex proceeded.

FIGS. 2-B and 2-C show scanning electron micrographs of the resulting catalyst. FIG. 2-B shows the state of the inner surfaces of the pores near the outside surface, and FIG. 2-C shows the state of the inner surfaces of the pores in the interior portion. It is clearly seen from these photographs that there was a nonuniform distribution of Ag grains within the catalyst particle.

FIG. 3 (broken line) shows the distribution of Ag within the catalyst particle. S of Ag in a portion measuring up to 6% by weight from the ouside surface layer of the catalyst particle toward its interior was 18.8%, and I in a portion measuring more than 60% by weight from the outside surface toward the interior was 12%. Hence, I/S was about 0.64. The foregoing results show that in contrast to the superheated steam heating, Ag deposited on the carrier was distributed nonuniformly in air heating.

The same reaction as in Example 1 was carried out using the resulting catalyst (Comparative Example 1). In the early stage of the reaction, $T_{40}$ was 217° C., and $S_{40}$ was 81.3%. After a continuous operation for three months, $T_{40}$ was 227° C., and $S_{40}$ was 79.8%. It is seen that in comparison with the catalyst of Example 2, the range of temperature rise was large, and the decrease of the selectivity was remarkable.

COMPARATIVE EXAMPLE 2

A catalyst having the same composition as the catalyst of Example 6 was prepared by repeating Example 6 except that heating for depositing $Na_2CO_3$ on the carrier was carried out by using air at 140° C. instead of using superheated steam at 140° C., and the final heating was carried out for 2 hours by using heated air at 300° C. instead of using superheated steam at 300° C. FIG. 2-D shows a scanning elecron micrograph (magnification 10,000×) of the resulting catalyst. It is seen that Ag grains were markedly agglomerated. The average diameter of the Ag particle was 0.4 micron, and their particle size ranged from 0.15 micron to 0.7 micron. The catalyst had a BET surface area of as low as 0.53 m²/g. The I/S within the catalyst particle was about 0.60, and the $I_{Na}/S_{Na}$ was about 0.22. Thus, it was confirmed that the distributions of Ag and Na within the catalyst particle were non-uniform.

When this catalyst was used in the same reaction as in Example 1, its performance was very low as shown by an oxygen conversion of 8% and a selectivity of 72% at 250° C.

EXAMPLE 9

A catalyst was prepared in the same way as in Example 1 except that the loading of barium was changed from 670 to 1700 ppm.

The performance of the catalyst was tested by using it in the same reaction as in Example 1 except that the reaction was carried out for 1 week at a bath temperature of 213° C. The oxygen conversion was 40%, and the selectivity of ethylene oxide was 81.6%. After the reaction, the catalyst had a BET surface area of 0.80 m²/g. During continuous operation for 1.5 months, the bath temperature was raised by 2° C. to maintain an oxygen conversion of 40%, but the selectivity did not change.

EXAMPLES 10-11

Example 9 was repeated except that the amount of Ba added and the source of Ba were changed as indicated in Table 3. The results obtained are shown in Table 3.

TABLE 3

| Example | Catalyst composition | Ba source | $T_{40}$ (°C.) | $S_{40}$ (%) |
|---|---|---|---|---|
| 10 | Ag: 13.5% Cs: 158 ppm | Ba(OH)$_2$ | 211 | 81.7 |
| 11 | Cl: 42 ppm Na: 0.4% Ba: 50 ppm | BaO$_2$ | 211 | 81.8 |

In this catalyst system, the addition of even a small amount of Ba evidently led to an increase in activity and selectivity.

What is claimed is:

1. A catalyst for the production of ethylene oxide from ethylene, said catalyst comprising a porous carrier composed of a molded article of a refractory material and having thereon (i) silver grains and (ii) as a cationic component, at least one alkali metal element selected from the group consisting of lithium, sodium, potassium, rubidium and cesium, wherein
- (A) silver is distributed on the outside surface of the carrier and on the inner surfaces of the pores of the carrier,
- (B) silver grains distributed on the inner surfaces of the pores of the carrier have an average diameter of 0.05 to 0.2 micron,
- (C) the loading (S) of silver on the outside surface layer of the catalyst and the loading (I) of silver on the innermost layer of the catalyst satisfy the following formula (1):

$$I \geq 0.7S \quad (1)$$

in which the said outside surface layer of the catalyst denotes a portion having a weight of about 5% by weight on average, in the range of about 4-6%, shaven as uniformly as possible from the ouside surface of one catalyst particle toward its inner layer when the weight of one catalyst particle is taken as 100%, and said innermost layer of the catalyst denotes an inner layer of the catalyst particle which is left after about 60% on the average, in the range of about 50 to 70%, has been shaven off from the outside surface of the catalyst particle toward its inner layer as uniformly as possible, and
- (D) the loading (Sc) of the alkali metal element as the cationic component on the outside surface layer of the catalyst and the loading (Ic) of the alkali metal element as the cationic component on the innermost layer of the catalyst satisfy the following formula (2-1) or (2-2):

$$Ic \geq 0.4Sc \quad (2\text{-}1)$$

in the case where the alkali metal is sodium or lithium $$Ic \geq 0.6Sc \quad (2\text{-}2)$$

in the case where the alkali metal is potassium, rubidium or cesium, in which said outside surface layer of the catalyst and said innermost layer of the catalyst are as defined above.

2. The catalyst of claim 1 in which as a cationic component, in addition to at least one of said alkali metal elements, barium is present on the porous carrier.

3. The catalyst of claim 1 or 2 in which the silver grains are present on the porous carrier in an amount of 5 to 20% by weight based on the entire catalyst.

4. The catalyst of claim 1 or 2 in which
- (i) in the case where sodium, as the alkali metal element, is present on the porous carrier, the total amount of sodium is 50 ppm to 1% by weight, and in the case where lithium is present on the porous carrier, the total amount of lithium is 0.1 to 1% by weight, based on the entire catalyst,
- (ii) in the case where potassium and/or rubidium, as the alkali metal element, is present on the porous carrier, the total amount of potassium and/or rubidium is not more than 0.1% by weight based on the entire catalyst, and
- (iii) in the case where cesium, as the alkali metal element, is present on the porous carrier, the amount of cesium is from 10 ppm to 0.5% by weight based on the entire catalyst.

5. The catalyst of claim 4 in which the silver grains are present on the porous carrier in an amount of 5 to 20% by weight based on the entire catalyst.

6. A process for producing a catalyst for the production of ethylene oxide from ethylene, which comprises
- (1) impregnating a porous carrier composed of a molded article of a refractory material with an aqueous solution containing an aqueous medium, a silver salt and an amine as a complex-forming agent,
- (2) heating the porous carrier with superheated steam in a condition where at least 30% by weight of the aqueous medium of said aqueous solution remains with the porous carrier, in such a manner as to at least substantially dry the aqueous medium and decompose the silver salt to deposit silver on the carrier, and
- (3) impregnating the carrier at least with an aqueous solution of a compound of at least one alkali metal element selected from the group consisting of lithium, sodium, potassium, rubidium and cesium as a cationic component simultaneously with the impregnation of the silver salt in step (1) above or with the deposition of silver in step (2) with regard to the porous carrier, or before or after either step (1) or (2), whereby said alkali metal compound is deposited on the carrier.

7. The process of claim 6 which comprises carrying out the heating and drying of the impregnated solution and decomposition of the silver salt with the superheated steam in such a manner as to satisfy the following formula (1) between the loadings (S) of silver on the outside surface layer of the catalyst and loading (I) of silver on the innermost layer of the catalyst:

$$I \geq 0.7S \quad (1)$$

and the following formula (2-1):

$$Ic \geq 0.4SC \quad (2\text{-}1)$$

in the case where the alkali metal is sodium or lithium, or the following formula (2-2):

$$Ic \geq 0.6Sc \quad (2\text{-}2)$$

in the case where the alkali metal is potassium, rubidium or cesium, in which the said outside surface layer of the catalyst denotes a portion having a weight of about 5% by weight on average, in the range of about 4-6%, shaven as uniformly as possible from the outside surface of one catalyst particle toward its inner layer when the weight of one catalyst particle is taken as 100%, and the said innermost layer of the catalyst denotes an inner layer of the catalyst particle which is left after about 60% on the average, in the range of about 50 to 70%, has been shaven off from the outside surface of the catalyst particle toward its inner layer as uniformly as possible.

8. The process of claim 6 or 7 in which step (2) is conducted with the superheated steam at a temperature of 120° to 500° C.

* * * * *